(12) United States Patent
Martin et al.

(10) Patent No.: US 6,469,201 B1
(45) Date of Patent: Oct. 22, 2002

(54) METHOD FOR PREVENTING, REMOVING OR REDUCING DEPOSITS IN APPARATUS PARTS DURING THE ESTERIFICATION OF ACRYLIC OR METHACRYLIC ACIDS

(75) Inventors: Friedrich-Georg Martin, Heidelberg (DE); Armin Schraut, Bensheim (DE); Josef Wekerle, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/147,836

(22) PCT Filed: Sep. 18, 1997

(86) PCT No.: PCT/EP97/05126

§ 371 (c)(1),
(2), (4) Date: Mar. 17, 1999

(87) PCT Pub. No.: WO98/12168

PCT Pub. Date: Mar. 26, 1998

(30) Foreign Application Priority Data

Sep. 18, 1996 (DE) .......................... 196 38 093

(51) Int. Cl.⁷ .................. C07C 69/52; C07C 69/48; B08B 7/00; B08B 9/00
(52) U.S. Cl. .................. 560/205; 560/218; 134/4; 134/22.14
(58) Field of Search ................. 560/205, 218; 134/4, 22.14

(56) References Cited

U.S. PATENT DOCUMENTS

| 4,600,795 A | * | 7/1986 | Frank et al. ............... 562/599 |
| 4,748,268 A | | 5/1988 | Pietsch et al. ............. 560/205 |
| 5,306,350 A | * | 4/1994 | Hoy et al. ................ 134/22.14 |
| 5,578,173 A | * | 11/1996 | Toot et al. .................... 203/6 |

\* cited by examiner

*Primary Examiner*—Alan L. Rotman
*Assistant Examiner*—Taylor V. Oh
(74) *Attorney, Agent, or Firm*—Oblon, Spivak, McClelland, Maier & Neustadt, P.C.

(57) ABSTRACT

In the preparation of esters of acrylic or methacrylic acid by esterification with alcohols, the interfering deposits formed on the apparatus parts by relatively high molecular weight by-products can be avoided, removed or lessened by allowing a liquid partly or wholly consisting of the alcohol used for the esterification to act on the deposits, fouled apparatus parts or on the surfaces of the apparatus parts on which deposits are easily formed, with preference being given to wetting the deposits or surfaces using suitable nozzles or cleaning sprayers.

5 Claims, No Drawings

METHOD FOR PREVENTING, REMOVING OR REDUCING DEPOSITS IN APPARATUS PARTS DURING THE ESTERIFICATION OF ACRYLIC OR METHACRYLIC ACIDS

The present invention relates to a method of avoiding, removing or lessening deposits on the surfaces of apparatus parts in the preparation of esters of acrylic or methacrylic acid by esterification of the corresponding acid with an alcohol.

It is known that esters of acrylic or methacrylic acid can be prepared industrially by catalyzed esterification of acrylic or methacrylic acid with the corresponding alcohols. This often results in the formation of relatively high molecular weight by-products which, inter alia, lead to deposits on the surfaces of the apparatuses used for the esterification reaction or down-stream apparatuses or apparatus parts, eg. on the trays of a separation column. The deposits lead to a restriction in function or a malfunction of the apparatuses and thus to a deterioration in the product quality of the reaction product, which makes cleaning of the corresponding apparatuses essential.

It has now been found that the corresponding deposits on the metal, glass, ceramic or plastic surfaces of the apparatuses or apparatus parts can be avoided, removed or lessened if a liquid comprising the alcohol used for the esterification or consisting of this alcohol is allowed to act on the deposits or the surfaces of the apparatuses or apparatus parts on which such deposits have formed or are easily formed.

The present invention accordingly provides a method of avoiding, removing or lessening deposits on the surfaces of apparatus parts used for the esterification reaction and/or downstream apparatus parts in the preparation of esters of acrylic or methacrylic acid by esterification of the corresponding acid with an alcohol having, in particular, from 1 to 4 carbon atoms, preferably in the presence of a strong acid such as sulfuric acid, p-toluene-sulfonic acid or acid ion exchangers, which comprises allowing a liquid partly or wholly consisting of the alcohol used for the esterification to act on the deposits or on the surfaces of the apparatus parts on which such deposits form. In general, the liquid should comprise at least 10 and in particular at least 50% by weight of the alcohol used for the esterification; it preferably consists essentially (entirely or virtually entirely) of the alcohol used for the esterification. However, cleaning the deposits from the apparatus surface in this way or lessening or avoiding such deposits does not succeed when using the corresponding ester formed in the esterification reaction, the acid used or water, but only when using the alcohol used in the esterification either alone or in combination with one or more of the above constituents.

It has been found to be extremely advantageous to use a nozzle or a plurality of nozzles or sprayers by means of which the entire surface of the relevant apparatus parts on which deposits have formed or easily form can be wetted or sprayed with the alcohol-containing liquid. This wetting by means of a nozzle or spraying of the apparatus surface can be carried out discontinuously or preferably continuously. It is thus possible to clean the surface of the relevant apparatuses or apparatus parts or to maintain a deposit-free surface so as to lead to a constantly high product quality of the reaction product. Suitable nozzles or sprayers are commercially available nozzles and sprayers such as center body nozzles, rotating spray nozzles and also wide-area cleaning sprayers. Preference is given to nozzles which produce alcohol droplets having a droplet diameter of less than 1 mm on the apparatus surface. It is noteworthy that the addition of a corresponding excess of alcohol to the esterification mixture produces no corresponding cleaning action.

Apparatuses or apparatus parts which have a tendency to suffer from deposits of relatively high molecular weight by-products are those which are used for the esterification reaction, but also the apparatuses and apparatus parts downstream of the actual esterification reaction, for example separation columns, which come into contact with the esterification mixture and are fouled by deposits and as a result of this cause, for example, a pressure drop in the trays of the column.

The following example and the comparative experiments are to illustrate the invention but do not restrict it in any way.

EXAMPLE 1

The esterification of methacrylic acid with methanol in the presence of p-toluenesulfonic acid was carried out in a reaction vessel having natural convection. A separation column having 20 trays was superposed on the reactor. The distance between the liquid surface and the lowest tray was 2.2 m. The column diameter was 0.8 m.

A commercial tangential solid center body nozzle was installed 30 cm below the lowest tray. At a continuous liquid throughput of 100 kg/hour of methanol through the nozzle, the entire underside of the tray could be wetted in this way. The methanol droplets produced had a droplet diameter of from 20 $\mu$m to 1 mm. The increase se in the pressure drop over the lowest tray of the column was employed as the measure for the degree of fouling of the column. The pressure drop increased by 1 mbar over a period of 10 days and then remained constant.

Comparative Experiment 1

The esterification reaction was carried out as in Example 1, but the nozzle was not installed. The corresponding amount of the methanol introduced through the nozzle in Example 1 was here added directly to the esterification mixture in the reactor. The pressure drop over the lowest tray of the column increased by 3 mbar over a period of 10 days and rose by a further 10 mbar over the course of the next 60 days.

Comparative Experiment 2

The esterification reaction was carried out as in Example 1, but the nozzle was not installed. Unlike Comparative Experiment 1, the amount of methanol introduced through the nozzle in Example 1 as not introduced into the esterification mixture in the reactor either. The pressure drop over the lowest tray of the column increased by 3 mbar over 10 days and rose by a further 10 mbar over the course of the next 60 days.

Comparative Experiment 3

The esterification reaction was carried out as in Example 1, but the apparatus parts were wetted by means of the nozzle using methyl methacrylate in place of methanol. The fouling of the separation column could not be avoided in this way. The pressure drop over the lowest tray of the column increased by 3 mbar over a period of 10 days and rose by a further 10 mbar over the course of the next 60 days.

We claim:

1. A method of avoiding, removing or lessening deposits on surfaces of apparatus parts in the preparation of esters of acrylic or methacrylic acid by esterification of the corresponding acid with an alcohol, comprising:

wetting said deposits, said surfaces of the apparatus parts or both, with a liquid comprising at least 10% by weight of the alcohol used for the esterification, wherein said wetting is performed using one or more nozzles or cleaning sprayers.

2. The method of claim 1, wherein the apparatus parts are parts of a separation column used for the esterification reaction or installed downstream of the separation column.

3. The method of claim 1, wherein said esterification is the esterification of methacrylic acid with methanol.

4. The method of claim 1, wherein said liquid consists essentially of the alcohol used for the esterification.

5. The method of claim 1, wherein said wetting step is performed continuously during the esterification process.

* * * * *